(12) United States Patent
Pfitzner et al.

(10) Patent No.: US 8,777,482 B2
(45) Date of Patent: Jul. 15, 2014

(54) DETECTING DEFECTS DURING LASER WELDING

(75) Inventors: Dieter Pfitzner, Weil der Stadt (DE); Tim Hesse, Ditzingen (DE); Winfried Magg, Ditzingen (DE)

(73) Assignee: TRUMPF Werkzeugmaschinen GmbH + Co. KG, Ditzingen (DE)

( * ) Notice: Subject to any disclaimer, the term of this patent is extended or adjusted under 35 U.S.C. 154(b) by 189 days.

(21) Appl. No.: 12/624,544

(22) Filed: Nov. 24, 2009

(65) Prior Publication Data
US 2010/0086003 A1    Apr. 8, 2010

Related U.S. Application Data

(63) Continuation of application No. PCT/EP2008/003302, filed on Apr. 24, 2008.

(30) Foreign Application Priority Data

May 26, 2007    (DE) .......................... 10 2007 024 789

(51) Int. Cl.
| | | |
|---|---|---|
| *G01N 25/72* | (2006.01) | |
| *G01K 17/00* | (2006.01) | |
| *B23K 26/03* | (2006.01) | |
| *B23K 26/32* | (2014.01) | |
| *B23K 31/12* | (2006.01) | |

(52) U.S. Cl.
CPC ............ *G01N 25/72* (2013.01); *B23K 26/3293* (2013.01); *B23K 2203/04* (2013.01); *B23K 2201/34* (2013.01); *B23K 26/034* (2013.01); *B23K 26/3206* (2013.01); *B23K 26/032* (2013.01); *B23K 31/12* (2013.01)
USPC ............... 374/5; 374/121; 374/29; 374/44; 374/141; 374/137; 702/35; 73/588; 219/121.63

(58) Field of Classification Search
USPC .......... 374/4, 5, 7, 43–45, 57, 120, 121, 129, 374/1, 141, 12; 250/338.1; 219/121, 6, 61, 219/121.62, 121.63, 121.78, 121.81, 219/121.82, 121.83, 121.85, 121.64; 700/166; 73/588; 702/35; 228/103, 104
See application file for complete search history.

(56) References Cited

U.S. PATENT DOCUMENTS 3,860,784 A * 1/1975 Brown et al. ............ 219/121.64
4,214,164 A   7/1980 Traub et al.
(Continued)

FOREIGN PATENT DOCUMENTS

DE          75933 A  *  9/1970
DE          4311320     10/1994
(Continued)

OTHER PUBLICATIONS

International Search Report from corresponding PCT Application No. PCT/EP2008/003302, mailed Aug. 27, 2008, 10 pages.
(Continued)

*Primary Examiner* — Gail Verbitsky
(74) *Attorney, Agent, or Firm* — Fish & Richardson P.C.

(57) ABSTRACT

A method for detecting defect in a weld seam during laser welding. The method includes performing a two-dimensionally locally resolved detection of radiation that is emitted by a solidified molten mass that is adjacent to a liquid melting bath. The method also includes determining at least one characteristic value for heat dissipation in the solidified molten mass by evaluating the detected radiation along at least one profile-section of the solidified molten mass, and detecting a defect in the weld seam by comparing the at least one characteristic value with at least one reference value.

10 Claims, 2 Drawing Sheets

(56) References Cited

U.S. PATENT DOCUMENTS

| | | | |
|---|---|---|---|
| 4,817,020 A | 3/1989 | Chande et al. | |
| 5,360,960 A * | 11/1994 | Shirk | 219/121.83 |
| 5,444,241 A | 8/1995 | Del Grande et al. | |
| 5,502,292 A * | 3/1996 | Pernicka et al. | 219/121.64 |
| 5,506,386 A | 4/1996 | Gross | |
| 5,552,575 A * | 9/1996 | Doumanidis | 219/124.34 |
| 6,188,041 B1 | 2/2001 | Kim et al. | |
| 6,822,188 B1 | 11/2004 | Kratzsch et al. | |
| 6,829,263 B1 * | 12/2004 | Richter et al. | 372/36 |
| 7,060,991 B2 * | 6/2006 | Reilly et al. | 250/443.1 |
| 7,479,616 B2 * | 1/2009 | Wang et al. | 219/121.64 |
| 7,620,233 B2 * | 11/2009 | Beck et al. | 382/152 |
| 7,959,353 B2 * | 6/2011 | Anantharaman | 374/4 |
| 2003/0165180 A1 * | 9/2003 | Weerasinghe et al. | 374/121 |
| 2004/0026389 A1 * | 2/2004 | Kessler et al. | 219/121.83 |
| 2004/0069754 A1 * | 4/2004 | Bates et al. | 219/121.63 |
| 2005/0169346 A1 * | 8/2005 | Murray et al. | 374/121 |
| 2005/0211687 A1 * | 9/2005 | Sonoda et al. | 219/137 R |
| 2005/0224472 A1 * | 10/2005 | Rasmussen et al. | 219/121.64 |
| 2005/0230364 A1 * | 10/2005 | Wang et al. | 219/121.64 |
| 2006/0006156 A1 * | 1/2006 | Huonker et al. | 219/121.64 |
| 2006/0011592 A1 * | 1/2006 | Wang et al. | 219/121.64 |
| 2006/0043078 A1 * | 3/2006 | Bernges et al. | 219/121.83 |
| 2007/0237201 A1 * | 10/2007 | Ignatowicz | 374/7 |
| 2010/0134628 A1 * | 6/2010 | Pfitzner et al. | 348/159 |
| 2011/0031226 A1 * | 2/2011 | Mokadem et al. | 219/121.64 |
| 2013/0126483 A1 * | 5/2013 | Dave et al. | 219/76.1 |
| 2013/0193123 A1 * | 8/2013 | Saint-Martin et al. | 219/121.63 |
| 2013/0220983 A1 * | 8/2013 | Haschke et al. | 219/121.81 |
| 2013/0228560 A1 * | 9/2013 | Ume et al. | 219/137 R |

FOREIGN PATENT DOCUMENTS

| | | | |
|---|---|---|---|
| DE | 4311320 A1 * | 10/1994 | |
| DE | 19505832 | 8/1996 | |
| DE | 19650883 | 6/1998 | |
| DE | 10160623 | 6/2003 | |
| DE | 10225450 A1 | 12/2003 | |
| DE | 10338062 | 4/2005 | |
| EP | 0554888 | 8/1993 | |
| EP | 0655294 | 5/1995 | |
| EP | 1326064 | 7/2003 | |
| EP | 1119436 | 9/2003 | |
| JP | 56041089 A * | 4/1981 | |
| JP | 01048678 A * | 2/1989 | |
| JP | 01083378 A * | 3/1989 | |
| JP | 2002337236 A * | 11/2002 | |
| JP | 2008000762 A * | 1/2008 | |

OTHER PUBLICATIONS

Notification of Transmittal of Translation of the International Preliminary Report in Patentability from the corresponding PCT Application No. PCT/EP2008/003302, issued Dec. 7, 2009, 5 pages.

Brueggermann et al., "Prediction of weld data using process control based on surface temperature measurement for high power energy flow processes", SPIE, col. 2888, pp. 168-177, downloaded from http://proceedings.spiedigitallibrary.org/ on Apr. 26, 2013.

* cited by examiner

DETECTING DEFECTS DURING LASER WELDING

CROSS-REFERENCE TO RELATED APPLICATIONS

This application is a continuation of and claims priority under 35 U.S.C. §120 to PCT/EP2008/003302, filed on Apr. 24, 2008, and designating the U.S., which claims priority under 35 U.S.C. §119 to German Patent Application No. 10 2007 024 789.5, filed on May 26, 2007. The contents of both the prior applications are hereby incorporated by reference in their entirety.

TECHNICAL FIELD

This invention relates to detecting defects in a weld seam during a laser welding operation.

BACKGROUND

When galvanized steel sheets are laser welded at an overlap joint, a defined gap is typically provided between the metal sheets so that resultant zinc vapors, which may disrupt the operation, can dissipate. In practice, that gap dimension between the metal sheets may not always be complied with in a reproducible manner. If the permissible gap dimension is exceeded by only a few tenths of a millimeter, a lack of fusion may be produced between the metal sheets. This lack of fusion is often referred to as a "false friend" because the weld seam, when viewed from outside, appears to be defect-free although there is no fusion between the metal sheets. It can be difficult to clearly detect a lack of fusion during the welding operation because that type of weld seam defect is predominantly inside the component or the weld seam and, as a result, indirect assessment variables may have to be used to detect certain defects.

In order to assess the quality of a weld seam during a laser welding operation, it is known to observe a solidified molten mass behind a liquid melting bath along the weld seam. For instance, U.S. Pat. No. 4,817,020 describes a process in which temperature is measured in real time at two or more mutually spaced apart locations of a solidified molten mass, and a cooling rate is established from the difference. Conclusions relating to the quality of the weld seam can be drawn from the cooling rate and interventions may optionally be made in the welding operation in order to optimize it.

It is further known from EP0655294 B1 to measure the temperature by means of high-speed pyrometers simultaneously and at both sides of a joint line at least at two locations behind a melting bath. Unlike temperature measurement at only one location, a clear association with process parameters of a welding operation can thereby be carried out. Point-like welding defects can further be detected at the measured locations.

In addition, the quality of a welding operation can also be assessed by monitoring a liquid melting bath of the welding operating. For instance, it is known, for example, from DE10338062A1, to monitor a liquid melting bath by means of a CCD camera during laser welding and to establish the relative, time-dependent movement of a front boundary face of the melting bath and a rear boundary face of a radiation surface of the laser. That measurement can be used to detect emissions from the melting bath.

It is further known from EP1119436A1 to establish the shapes of mutually spaced-apart maximum intensity regions and a minimum region of high-energy radiation, for example, plasma or laser radiation, which is located therebetween and to compare it with predetermined shapes in order thereby to control or adjust the material processing operation. The shapes of the spaced-apart maximum intensity regions and the minimum region of high-energy radiation can be established by technical measurements in a vapor capillary vessel.

SUMMARY

In general, this invention relates to detecting defects in a weld seam during a laser welding operation.

One aspect of the invention provides a method for detecting defects in a weld seam during laser welding. The method includes performing a two-dimensionally locally resolved detection of radiation that is emitted by a solidified molten mass that is adjacent to a liquid melting bath. The method also includes determining at least one characteristic value for heat dissipation in the solidified molten mass by evaluating the detected radiation along at least one profile-section of the solidified molten mass, and detecting a defect in the weld seam by comparing the at least one characteristic value with at least one reference value.

A thermal image of the solidified molten mass or the weld seam directly adjacent to the liquid melting bath provides information concerning the fusion between a pair of metal sheets being welded together to form a component. In the event of complete material connection between the metal sheets, cooling occurs comparatively quickly owing to thermal conduction in both metal sheets. If there is a lack of fusion, thermal flux into the component is disrupted and, as a result, the weld seam remains hot for a longer time in the event of the occurrence of a "false friend". Therefore, it is possible for lack of fusion to be detected by the local or temporal heat dissipation into the component being evaluated because the thermal gradient of the cooling weld seam changes significantly.

Since the laser beam is normally moved over the component at a constant speed, a substantially stationary temperature field is formed around a processing surface. The temporal progression of the heat dissipation into the component can therefore be established by a locally resolved measurement. A two-dimensionally locally resolved measurement allows very reliable measurement values to be obtained.

In addition, the detection of through penetration (burn-through) is further possible since a portion of the laser energy is radiated at the lower side of the component during the through penetration and is not introduced into the component. As a result, when there is through penetration, the cooling rate of the weld seam remains substantially constant when the laser power is increased from a given laser power.

In some embodiments, only an intensity portion of the detected radiation that is not caused by background radiation is taken into consideration when determining the characteristic value. Owing to the locally resolved measurement, it is possible to subtract the background radiation from the characteristic profile of the overall radiation detected, and, thus, the intensity portion of the background radiation can remain unconsidered when the characteristic value is determined. It is also possible to take local fluctuations in the background radiation into consideration when the intensity portion is established.

In some cases, the detected radiation is evaluated along at least two thermal profile-sections that are spaced apart from each other and which extend substantially perpendicularly relative to the weld seam. One of the two profile-sections is selected so as to be directly behind the melting bath and at least a second one is selected at a defined distance so as to be relatively far from the molten mass. The distribution of the thermal radiation perpendicular to the weld seam is evaluated at each of the profile-sections so that the hottest location of the weld seam, that is to say, the maximum of the distribution, can be established. The detection of the hottest location can help to increase the reliability of the measurement in comparison with the detection of individual locations over the weld seam. For the evaluation, a quotient can be calculated from the maximums of the profile-sections. A lack of fusion can be inferred when the quotient exceeds a reference value or when the reciprocal value of the quotient falls below a reference value. The reference value can be application-specific and can be established in an experimental manner. Alternatively or in addition, the detection of lack of fusion with reference to the profile half-value width can be carried out in a similar operation.

In some embodiments, the characteristic value is determined from profile heights of the profile-sections which extend perpendicularly relative to the weld seam. It is possible to determine the profile height, that is to say, the distance of the maximum of the distribution in relation to the background radiation, from the distribution of the thermal radiation along each profile-section. Unlike the determination of the characteristic value by quotient formation of the intensity values of the maximums, only the intensity portion not caused by the background radiation is taken into consideration when the quotient is formed from the profile heights.

It is further possible to obtain additional information concerning the weld seam based on an asymmetry of the profile-sections, which indicate an asymmetrical dissipation of heat into the component. Asymmetrical heat dissipation makes defective lateral seam positioning detectable, given identical thickness and type metal sheet, when an I seam is welded at the butt joint. This case may occur, for example, during tailored blank, profile, and longitudinal and transverse tube welding.

In some cases, the detected radiation is evaluated along a profile-section that extends substantially parallel with the welding direction, preferably on the axis of symmetry of the weld seam. The radiation intensity along that profile-section has a characteristic progression for the heat dissipation into the component. The radiation intensity along the profile-section corresponds to the pixel brightness of the thermal image, which may be detected with a camera.

In some embodiments, the characteristic value is determined based on a comparison between the progression of the radiation intensity along the profile-section and a model progression for the radiation intensity. The progression of the radiation intensity along the profile-section can be described with a mathematical model, for example, an exponential function $$I=B*\exp(C*X)-A$$

where I denotes the radiation intensity, A denotes the portion of background radiation (taken to be homogeneous), X denotes the position along the profile-section, and the adaptation coefficients "B" and "C" represent characteristic values for the heat transport into the workpiece. If a lack of fusion occurs, coefficient "B" becomes greater and coefficient "C" becomes substantially smaller. The quality of the adaptation of the exponential function to the thermal track of the weld seam can be described in this instance by means of a suitable quantity such as, for example, by means of the total of the error squares (so-called chi-square errors). In the event of successful adaptation, that characteristic value has small numerical values for each camera image. If locally high chi-square errors are established in a weld seam progression or in a chronological sequence of images, this indicates local disruptions of the heat track, such as, for example, a hole in the component.

It is also possible to measure a plurality of profile-sections at different locations along the weld seam and thereby to establish the hottest location of the weld seam. Generally, the hottest locations of the weld seam should extend along the axis of symmetry. In the case of asymmetrical welding, however, those locations may also be distributed around the axis of symmetry. The exponential function (above) can then be adapted to the maximums of the profile-sections obtained in that manner and the adaptation coefficients can be established therefrom.

In some cases, the method also includes performing a locally resolved detection of radiation emitted by the liquid melting bath. Information obtained from the detected radiation emitted by the liquid melting bath can be used to determine the location of a boundary between the solidified molten mass and the liquid melting bath. For the purpose of detecting radiation emitted by the liquid melting bath, the profile-section can be extended in the welding direction from the region of the solidified molten mass into the region of the liquid molten mass. A deviation in the brightness signal will be visible at the phase transition from liquid to solid. The melting bath end can thus be detected by calculating the intersection of a mean straight line in the liquid region with the exponential function in the solidified region. The detection of the melting bath end can be used for static or dynamic positioning of the first profile-section directly behind the melting bath end.

Another aspect of the invention features a method for detecting defects in a laser welding operation that includes performing a two-dimensionally locally resolved detection of radiation emitted by a liquid melting bath that has a processing region (e.g., a radiation surface). The method also includes evaluating the detected radiation in order to locate a minimum intensity region of the liquid melting bath and detecting a defect in the weld seam based on the location and/or the intensity of the minimum intensity region.

A maximum intensity region that is caused by the laser radiation surface is generally visible during welding at the overlap joint. In some cases, a small minimum intensity region, representing a capillary opening, may be located inside the laser radiation surface. The term minimum or maximum intensity region is intended to refer to a region whose radiation intensity is below or above the radiation intensity of the remainder of the liquid melting bath. The following explanations do not relate to the small minimum intensity inside the laser radiation surface but instead to a comparatively large minimum intensity region that is behind the maximum intensity region of the laser radiation surface in relation to the direction of processing. It has been found that conclusions concerning weld defects can be drawn from the properties of that minimum intensity region.

In some embodiments, a distance between a rear edge of the radiation surface and a front edge of the minimum intensity region is compared with a limit distance in order to detect a lack of fusion. It is possible to assume a good material connection between the metal sheets if the surface-area of the minimum intensity region overlaps the laser radiation surface. If the minimum intensity becomes separated from the laser radiation surface, a lack of fusion can be inferred. Thus, the seam quality can be assessed by evaluating the distance of a predominant front edge of the minimum intensity region or a front edge, which is interpolated from the shape of the minimum intensity, relative to the rear edge of the radiation surface. Overlapping indicates a material connection between the metal sheets. A lack of fusion is diagnosed in the event of a distance which exceeds a definable limit distance. The limit distance can be established by test welds and may also assume the value zero or negative values in individual cases so that a lack of fusion is immediately detected when the minimum intensity region becomes separated from the radiation surface.

In some cases, a lack of fusion in the weld seam is detected when a minimum intensity region is not found. The minimum intensity behind the laser radiation surface is indicative of a melting bath deficiency owing to a gap between the metal sheets. That melting bath deficiency appears when the initially separate molten masses of the upper sheet and lower sheet become joined behind the laser radiation surface to form a common melting bath. The gap is in this case bridged and there is produced a material connection between the metal sheets. If the molten masses of the upper sheet and lower sheet do not become joined, however, the radiation maximum and, where applicable, the known capillary opening is visible during the welding substantially within the known laser radiation surface. The minimum intensity behind the laser radiation surface disappears at that time, which is indicative of a lack of fusion. In that case, the individual molten masses of the upper sheet and lower sheet solidify separately and the so-called "false friend" is produced.

In some embodiments, the radiation intensity of the minimum intensity region can be compared with a reference value in order to detect a through penetration defect. The relative brightness of the minimum intensity region can be indicative of a though penetration. For example, a dark minimum intensity indicates a continuous "hole" within the melting bath deficiency and therefore though penetration. A relatively bright minimum intensity indicates a closed melt film of the lower sheet or accordingly a connection only owing to welding. The evaluation of the relative brightness of the minimum intensity is carried out by comparison with reference measurements or with adjacent brightness values of the surrounding molten mass.

In some embodiments, the method can also include performing a two-dimensionally locally resolved detection of radiation emitted by a solidified molten mass adjacent to the liquid melting bath, and determining at least one characteristic value for heat dissipation in the solidified molten mass by evaluating the radiation detected from the solidified molten mass. In this case, detecting the defect in the weld seam can also include comparing the at least one characteristic value with at least one reference value.

Measurements from the liquid molten mass (e.g., the detected radiation of the liquid molten mass) that are received during the welding operation can supply a prediction concerning defects and may not be indicative of changes in the weld seam resulting from changes in the solidifying molten mass during cooling. More extensive information concerning lack of fusion, can be obtained from the region of the solidified molten mass directly adjacent to the liquid molten mass being observed. The combined evaluation of the liquid molten mass and the solidified molten mass can be used to verify whether a weld seam defect that is predicted during the monitoring of the molten mass near the capillary occurs at the same location in the cooling weld seam. Highly reliable monitoring of the operation can thereby be achieved by means of a combined evaluation of geometric characteristics from the liquid molten mass near the capillary and thermographic data from the solidified molten mass.

In some cases, an intervention is made in the welding operation after a defect is detected in the weld seam and it is thereby possible to control the welding operation. In this instance, it is possible to influence welding parameters such as welding speed, radiation intensity, clamping forces, etc., in order to improve the quality of the welding.

In some embodiments, a locally resolving detector for visible radiation, near infrared, mid infrared or far infrared is used for locally resolved detection of the radiation. Suitable detectors (i.e., measuring devices) include CCD cameras, CMOS cameras, photodiode arrays, InGaAs thermocameras, and quotient pyrometry measuring devices. In some cases, a combination of different detectors can be used. Quotient pyrometry measuring devices can establish the temperature in the monitored region in a locally resolved manner by simultaneously measuring the radiation emitted at two different wavelengths. In some cases, a combination of different detectors can be used. As set out above, two detection regions of the process zone can be used to detect a lack of fusion or a through penetration defect: the region of the liquid molten mass near the capillary and the region of the solidified molten mass. A single measuring device (e.g., a camera) can be arranged coaxially relative to the laser beam in order to monitor both the region of the molten mass near the capillary and the region of the solidified molten mass. Alternatively, the region of the solidified molten mass can be detected with a camera which is arranged at an angle relative to the laser beam.

In some cases, the emitted radiation is detected in a near infrared wavelength range, e.g., between 1 µm and 2 µm, in a two-dimensionally locally resolved manner. The 1 µm and 2 µm wavelength range is suitable for detecting the thermal radiation of the solidified molten mass. Radiation in the 1 µm and 2 µm wavelength range can simultaneously also be used to observe the liquid molten mass. Additionally or alternatively, radiation in other wavelength ranges, for example, in the visible range, can also be detected in a locally resolved manner, e.g., to evaluate the geometry of the liquid melting bath.

Other aspects, features, and advantages are in the description, drawings, and claims.

DETAILED DESCRIPTION

Figure 1A:
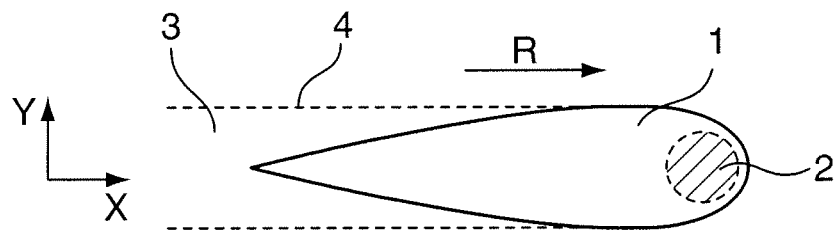
FIGS. 1a-1c are schematic illustrations of a liquid melting bath during a welding operation.

FIG. 1a shows a liquid melting bath 1 that is produced, for example, during laser welding of galvanized metal sheets at an overlap joint around. The liquid melting bath 1 includes a processing region (e.g., a radiation surface 2), at which a vapor capillary is formed. During a welding operation, the radiation surface 2 is moved at a constant speed over the metal sheets to be welded in a welding direction R, which corresponds to the X direction of an X-Y coordinate system. A solidified molten mass 3 forms a weld seam 4 between the metal sheets. The solidified molten mass 3 adjoins the liquid melting bath 1 counter to the welding direction R.

Figure 2:
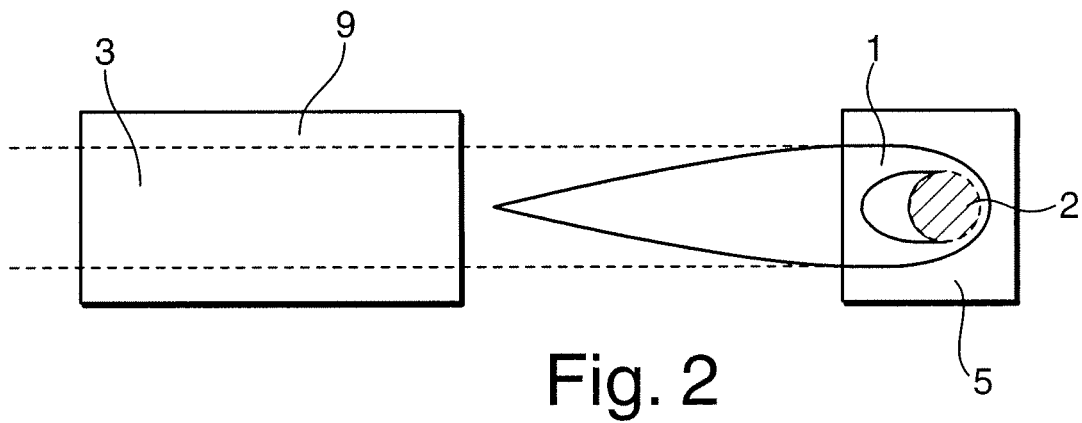
FIG. 2 is a schematic illustration of the liquid melting bath of FIG. 1c with an adjacent, solidified molten mass and two detection regions.

When galvanized metal sheets are laser welded, a lack of fusion between the metal sheets may be produced at an overlap joint. When viewed from outside, the weld seam 4 may appear to be defect-free at the location of the lack of fusion even though no connection exists between the metal sheets. In order to detect such a lack of fusion or other defects in the weld seam 4, a locally resolved measurement (e.g., a two-dimensional image) of the emitted radiation can be taken, as shown in FIG. 2, in a first detection region 5 that contains a portion of the melting bath 1 with the radiation surface 2. The two-dimensional image can be taken with a camera in a substantially coaxial manner relative to the laser beam. The radiation intensity measured in the first detection region 5 has a maximum intensity region within the radiation surface 2. The radiation intensity is higher at the maximum intensity region than in the surrounding liquid melting bath 1.

During welding at the overlap joint, a minimum intensity region 6 (FIG. 1b) is generally formed behind the radiation surface 2 a minimum intensity region 6 during welding at the overlay joint. The minimum intensity region 6 can be found by means of the locally resolved measurement. The minimum intensity region 6 behind the laser radiation surface 2 can be indicative of a melting bath deficiency owing to a gap between the metal sheets. That melting bath deficiency appears when the molten masses of the upper sheet and lower sheet become joined behind the laser radiation surface 2. The gap is then spanned and a material connection between the metal sheets is produced. If the molten masses of the upper sheet and lower sheet do not become joined, however, substantially only the radiation surface 2 with the radiation maximum and optionally the capillary opening is visible during the welding operation and the minimum intensity region 6 disappears behind the laser radiation surface 2, as shown in FIG. 1a. If that is the case, it may be assumed that there is a lack of fusion in the weld seam 4.

Figure 1B:
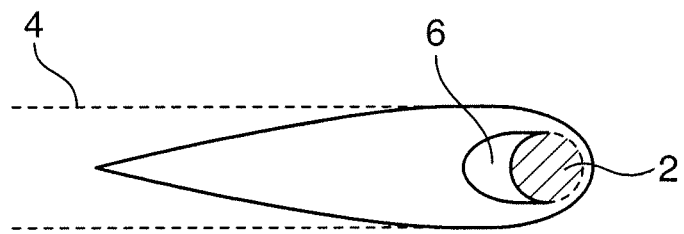
Figure 1C:
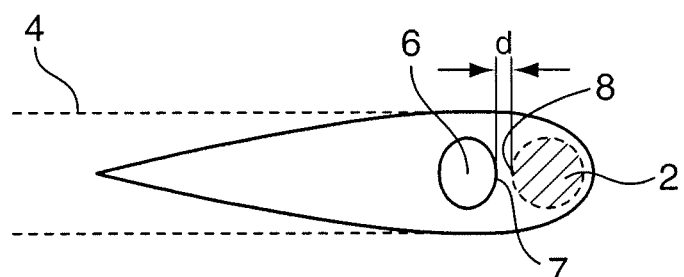

Good material connection between the metal sheets may be assumed if the minimum intensity region 6 overlaps the laser radiation surface 2, as shown in FIG. 1b. However, a lack of fusion can be inferred if the minimum intensity region 6 becomes separated from the laser radiation surface 2, as shown in FIG. 1c. By evaluation of the distance d of a predominant front edge 7 or a front edge 7 of the minimum intensity region 6 interpolated from the shape of the minimum intensity relative to the rear edge 8 of the radiation surface 2, it is possible to assess the quality of the weld seam 4. A lack of fusion is diagnosed in the event of a distance d that exceeds a definable limit distance which is established by test welds.

In addition to the detection of lack of fusion, it is also possible for the image taken in the first detection region 5 to be used to detect a through penetration defect. To detect a through penetration defect, the radiation intensity in the minimum intensity region 6 is compared with a reference value which is established during reference measurements. To that end, the relative brightness of the minimum intensity at the center of the minimum intensity region 6 can be compared to the surrounding molten mass or to a fixed value as a characteristic value. A minimum intensity region that is dark (i.e., less radiation intensive) is indicative of a continuous "hole" or a capillary and therefore through penetration. A minimum intensity region that is lighter (i.e., more radiation intensive) is indicative of a closed molten film of the lower sheet or accordingly a connection in the case of welding into the lower sheet.

Generally, both lack of fusion and through penetration can be detected by observing the melting bath 1 in the first detection region 5. The signals received in the liquid melting bath 1 during the welding operation provide a prediction of defects and naturally may not be indicative of changes in the weld seam 4 that are produced as a result of changes in the solidified molten mass 3 during cooling. However, it is also possible to detect the radiation emitted by the solidified molten mass 3 in a two-dimensionally locally resolved manner in a second detection region 9 (FIG. 2) in order to establish one or more characteristic values for the heat dissipation in the solidified molten mass 3. Subsequently, defects in the weld seam 3 can be established by comparing the characteristic value with a reference value.

Two possible variants for measuring and evaluating the local or temporal heat dissipation into the component are explained below by way of example, in both cases profile-sections, that is to say, one-dimensional sections in the two-dimensional radiation distribution of the radiation detected in the second detection region 9 being evaluated. By restricting the evaluation of the measured radiation to one or more profile-sections, it is possible to carry it out in an accelerated manner in comparison with evaluation of the complete two-dimensional distribution for detection of weld seam defects so that the detection can be carried out in real time.

Figure 3:
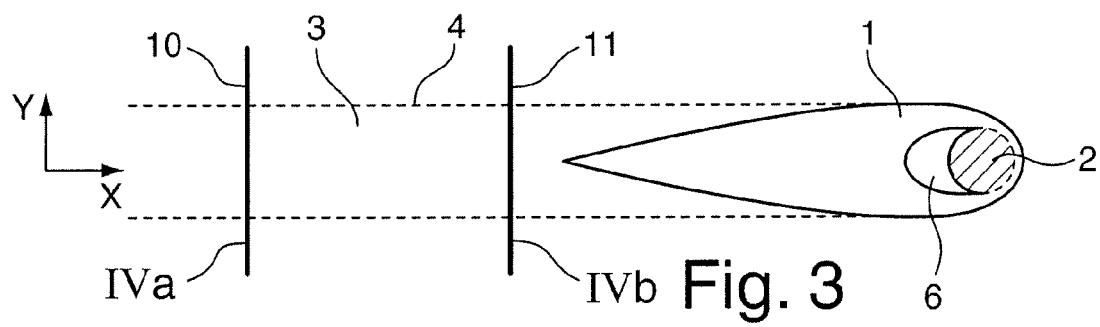
FIG. 3 is a schematic illustration of the liquid melting bath of FIG. 1c showing an adjacent, solidified molten mass with two profile-sections that extend perpendicularly relative to the weld seam.
Figure 4A:
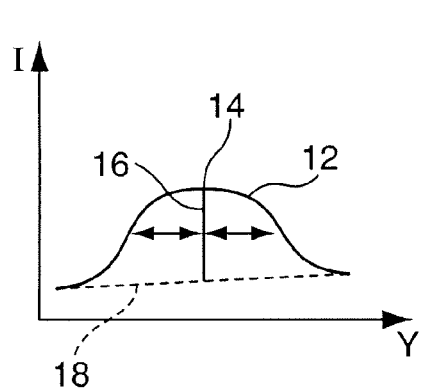
FIGS. 4a and 4b are schematic illustrations of the intensity distributions of the detected radiation along the profile-sections of FIG. 3.
Figure 4B:
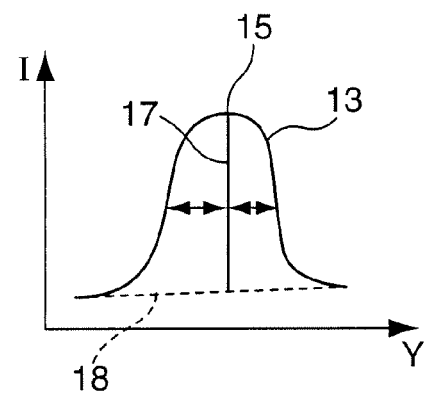

In order to explain the first variant, the position of two profile-sections 10, 11 in the solidified molten mass 3 of the weld seam 4 is shown in FIG. 3. The profile-sections 10, 11 extend perpendicularly relative to the weld seam 4, that is to say, in a Y direction of an XY co-ordinate system, with spacing of 4.5 mm from each other. A first profile-section 10 is arranged at a relatively large distance from the melting bath 1 and a second profile-section 11 is arranged almost directly behind the melting bath 1. In FIGS. 4a and 4b, the associated intensity distributions of the detected radiation 12, 13 along the profile-sections 10, 11 are set out. The radiation intensity is substantially normally distributed about a maximum 14, 15. Half-value widths of the distributions are illustrated by double-headed arrows. In order to establish a characteristic value for the heat dissipation between the profile-sections 10, 11, a quotient can be formed from the maximums 14, 15 of the intensity distributions 14, 15. Alternatively, the quotient can be established from the profile heights 16, 17, that is to say, the differences between the maximums 14, 15 and intensity lines of the background radiation 18, 19 that are inclined slightly upwards in the Y direction. The intensity lines of the background radiation 18, 19 are established in this instance in that the progression of the intensity distributions 12, 13 of the total radiation is followed up to the edges of the normal distribution and these are connected by a straight line. It is thereby possible that the portion of the background radiation 18, 19 that is produced by the slight ascent of the intensity lines in the Y direction is not taken into consideration for establishing the characteristic value.

In order to establish a lack of fusion, the quotient is compared with a reference value. The heat dissipation into the component progresses comparatively quickly if there is complete fusion between the metal sheets. A lack of fusion between the metal sheets brings about slower thermal flux into the component so that it is possible to conclude that such a defect is present if the calculated quotient exceeds the reference value or if the reciprocal value of the quotient falls below the reference value. The reference value is application-specific and can be established by experiment.

The half-value width of the profile-sections may be evaluated as an alternative or optionally additional characteristic. The half-value width of the second profile-section 12 is naturally significantly wider in comparison with the first profile-section 11 owing to the lateral heat dissipation into the component. The evaluation of the half-value width is can be carried out as previously described by means of quotient formation and can also be used as an assessment characteristic.

It is further possible to obtain additional information concerning the weld seam from an occurrence of asymmetry of the intensity progressions 12, 13, which indicates asymmetrical heat dissipation into the component. Provided that the sheet thickness and type are identical, a defective lateral seam positioning becomes visible when an I seam is welded at a butt joint with reference to asymmetrical heat dissipation. This case may occur, for example, in applications in sheet metal welding, such as tailored blank, profile welding, and longitudinal and transverse tube welding.

It is further possible to detect through penetration with the above method. A portion of the laser energy is emitted at the lower side of the component during penetration welding and is not introduced into the component, and, as a result, the cooling rate of the weld seam 4 remains constant during penetration welding over its progression in the X direction, which can also be detected as described above. It will be understood that the radiation image in the second detection region 9 can also be evaluated at more than only two profile-sections. In that case, a quotient which is compared with a reference value is established between profile-sections which are adjacent to each other and/or spaced further apart, conclusions being drawn with regard to a defect of the weld seam 4 from a plurality of those comparisons.

Figure 5:
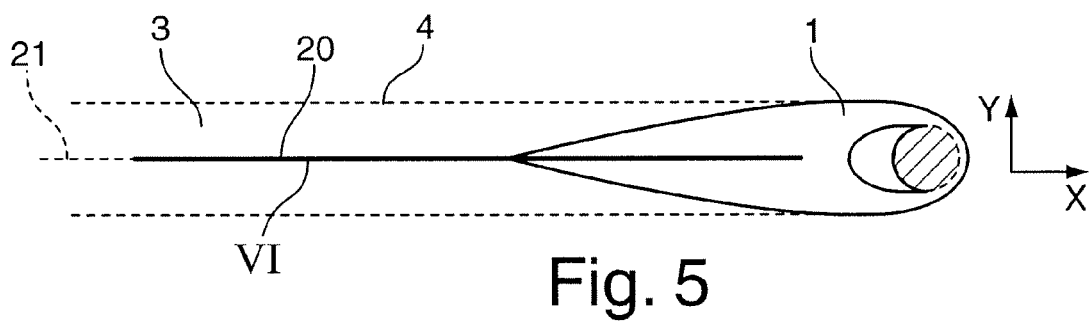
FIG. 5 is a schematic illustration of the liquid melting bath of FIG. 1c with a profile-section that extends along an axis of symmetry of the weld seam.
Figure 6:
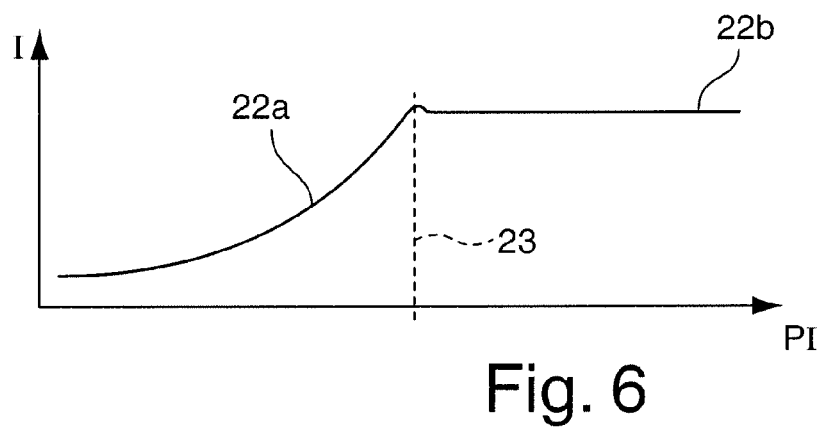
FIG. 6 is a schematic illustration of an intensity distribution of detected radiation in the profile section of FIG. 5.

In the second measurement and evaluation variant which is explained with reference to FIG. 5, a single profile-section 20 is evaluated along an axis of symmetry 21 of the weld seam 4. An intensity progression of the radiation 22a, 22b detected in the X direction is illustrated in FIG. 6.

The intensity I along the profile-section 20, which corresponds to the pixel brightness of an image which is taken with a camera, has a characteristic progression that can be described with a mathematical model, for example, an exponential function $$I = B^* \exp(C^* X) - A \quad (1)$$

The adaptation coefficients "B" and "C" are characteristics for the heat transport into the workpiece and A constitutes the portion of background radiation. When a lack of fusion occurs, coefficient "B" becomes greater and coefficient "C" becomes substantially smaller. The quality of the adaptation of the exponential function from equation (1) to the intensity distribution of the radiation 22a that is detected along the axis of symmetry 21 of the weld seam 4 in the solidified molten mass 3 is described by means of the sum of the error squares in the form of the chi-square error. If adaptation is successful, that characteristic value has small numerical values for each camera image. If high chi-square errors are established locally in a weld seam progression or in the image sequence, this is indicative of local disruptions of the heat track, such as, for example, a hole in the component.

In order to further increase the reliability of the measurement, a profile-section can further be measured, in accordance with the measurement variant described above with reference to FIG. 3 and FIG. 4, at a plurality of locations of the weld seam 4 perpendicularly relative thereto, and the hottest location of the weld seam 4 can thereby be established. The exponential function from equation (1) can then be adapted to the measurement values obtained in this manner and the adaptation coefficients can accordingly be established.

The profile-section 20 is not limited to the region of the solidified molten mass 3 along the axis of symmetry 21 of the weld seam 4, but instead can also extend into the region of the liquid melting bath 1. The intensity of the radiation 22b detected in the region of the liquid molten mass 1 extends in a substantially constant manner so that the phase transition from liquid to solid can be detected at a boundary 23 by a deviation in the brightness signal owing to a jump of the spectral emission level. By calculation of the intersection of a straight compensation line of the intensity of the radiation 22b detected in the liquid region with the exponential function from equation (1) which characterizes the intensity of the detected radiation 22a in the solidified region, the boundary 23 and therefore the end of the melting bath 1 can consequently be detected.

An evaluation can be carried out at both the first detection region 5 and the second detection region 9 in the manner described above. The combined evaluation can be used to verify whether a weld seam defect that is detected during the Monitoring of the melting bath 1 near the capillary occurs at the same location in the cooling weld seam 4. By ensuring the weld defect detection by means of a combined evaluation of geometric characteristics from the melting bath 1 near the capillary and thermographic data from the solidified molten mass 3, a high level of reliability of process monitoring is thereby achieved. The welding operation can also be controlled based on the measurement values obtained, such as by intervening in the welding operation by varying the beam strength or the welding speed, or intervening in the technical system (e.g., by adjusting clamping forces).

In order to detect the radiation emitted in a two-dimensionally locally resolved manner, it is possible to use locally resolving detectors for the visible or near-to-far infrared range. Suitable detectors include CCD or CMOS cameras, photodiode arrays, InGaAs thermocameras, and quotient pyrometry measuring devices. The detector or detectors can be configured to detect radiation in the near infrared range (e.g., between 1 μm and 2 μm). A combination of different types of detectors can also be used. When the detector is arranged coaxially relative to the laser beam, both the first and the second detection region 5, 9 can be monitored with the same device (i.e., the detector). Alternatively, it is possible to detect the second detection region 9 for monitoring the solidified molten mass 3 with a first camera that is arranged at an angle relative to the laser beam while the first detection region 1 is detected with a second camera that is orientated coaxially relative to the laser beam.

Although the above-described methods have been illustrated with reference to a welding operation at the overlap joint of galvanized metal sheets, it will be appreciated that they can also advantageously be used in other welding operations in order to detect welding defects, in particular lack of fusion, weld-in defects or through penetration defects, lateral seam displacement or local omissions, such as holes in the weld seam.

A number of embodiments of the invention have been described. Nevertheless, it will be understood that various modifications may be made without departing from the spirit and scope of the invention. Accordingly, other embodiments are within the scope of the following claims.

What is claimed is:

1. A method for detecting defects in a weld seam during a laser welding operation, the method comprising:

performing a two-dimensionally locally resolved detection of radiation intensity emitted by a solidified molten mass adjacent to a liquid melting bath;

evaluating the detected radiation intensity along two profile-sections which are spaced apart from each other and extend substantially perpendicularly relative to the weld seam, and determining a maximum radiation intensity, profile height, or half-value width of each profile-section;

determining a characteristic value for heat dissipation in the solidified molten mass, wherein the characteristic value is indicative of a comparison of the maximum radiation intensities, the profile heights, or the half-value widths of the two profile-sections; and detecting a defect in the weld seam by comparing the characteristic value with a reference value established by test measurements.

2. The method of claim 1, wherein performing the two-dimensionally locally resolved detection of radiation intensity emitted by the solidified molten mass comprises capturing a two-dimensional image of the solidified molten mass.

3. The method of claim 1, wherein the characteristic value is determined based on an asymmetry of at least one of the profile-sections.

4. The method of claim 1, wherein the two-dimensionally locally resolved detection of radiation intensity is performed using a CCD camera, a CMOS camera, or an InGaAs thermocamera.

5. The method of claim 1, wherein the detected radiation intensity is within a near infrared wavelength range.

6. The method of claim 5, wherein the detected radiation intensity is within a wavelength range of about 1 µm to about 2 µm.

7. The method of claim 1, wherein the characteristic value for heat dissipation is determined by forming a quotient from the maximum radiation intensities, the profile heights or the half-value widths of the two profile-sections.

8. A method for detecting defects in a weld seam during a laser welding operation, the method comprising:

performing a two-dimensionally locally resolved detection of radiation intensity emitted by a solidified molten mass adjacent to a liquid melting bath;

evaluating the detected radiation intensity along a profile-section extending along the weld seam for determining a characteristic value of a thermal gradient of the weld seam as the weld seam is allowed to cool, wherein the characteristic value is calculated by adapting an exponential function $I=B\times\exp(C\times X)-A$ to the detected radiation intensity and determining the adaptation coefficients B and/or C of the exponential function, wherein the characteristic value comprises B and/or C; and detecting a defect in the weld seam by comparing the characteristic value of the thermal gradient of the cooling weld seam with a reference value established by test measurements.

9. The method of claim 8, wherein the profile-section extends along an axis of symmetry of the weld seam.

10. The method of claim 8, wherein performing the two-dimensionally locally resolved detection of radiation intensity emitted by the solidified molten mass comprises capturing a two-dimensional image of the solidified molten mass.

* * * * *